(12) United States Patent
Tsuruta et al.

(10) Patent No.: US 11,076,744 B2
(45) Date of Patent: Aug. 3, 2021

(54) METHOD OF MANUFACTURING ENDOSCOPE AND ENDOSCOPE

(71) Applicant: OLYMPUS CORPORATION, Tokyo (JP)

(72) Inventors: Teppei Tsuruta, Hino (JP); Kenichi Nishina, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 695 days.

(21) Appl. No.: 15/846,423

(22) Filed: Dec. 19, 2017

(65) Prior Publication Data

US 2018/0125334 A1 May 10, 2018

Related U.S. Application Data

(63) Continuation of application No. PCT/JP2016/085634, filed on Nov. 30, 2016.

(30) Foreign Application Priority Data

Feb. 3, 2016 (JP) .............................. JP2016-018919

(51) Int. Cl.
*A61B 1/00* (2006.01)
*A61B 8/12* (2006.01)
(Continued)

(52) U.S. Cl.
CPC ........ *A61B 1/0011* (2013.01); *A61B 1/00114* (2013.01); *A61B 1/012* (2013.01);
(Continued)

(58) Field of Classification Search
CPC ......... B29C 65/02; B29C 65/68; B29C 61/02; B29C 61/025; B29C 63/0069; A61B 1/00043; A61B 1/0011; A61B 1/00114
(Continued)

(56) References Cited

U.S. PATENT DOCUMENTS

2002/0062082 A1* 5/2002 Ohara .................. A61B 8/4416 600/462
2002/0147385 A1* 10/2002 Butler ................ A61B 1/00137 600/114
(Continued)

FOREIGN PATENT DOCUMENTS

CN 104812290 A 7/2015
CN 104837398 A 8/2015
(Continued)

OTHER PUBLICATIONS

International Search Report dated Feb. 21, 2017 issued in PCT/JP2016/085634.
(Continued)

*Primary Examiner* — Aaron B Fairchild
(74) *Attorney, Agent, or Firm* — Scully, Scott, Murphy & Presser, P.C.

(57) ABSTRACT

A method of manufacturing an endoscope includes: dividing some of signal lines into bundle portions; notching a part of a tube to form one or a plurality of notch portions; cutting at least one end portion of the tube in a state where the tube is folded with each notch portion to produce a first heat-shrinkable tube having cylindrical portions with aligned end portions in longitudinal directions of the cylindrical portions; inserting the divided bundle portions into the cylindrical portions of the first heat-shrinkable tube, respectively; inserting the signal lines into a second heat-shrinkable tube; heating at least an overlapping portion in a state where the first and second heat-shrinkable tubes partially overlap each other to cause heat shrinkage; inserting the signal cable and the channel into a tubular portion; and connecting the tubular portion to a distal end constituting portion to form the insertion portion.

6 Claims, 15 Drawing Sheets

(51) Int. Cl.
*A61B 1/012* (2006.01)
*A61B 1/018* (2006.01)
*A61B 1/05* (2006.01)
*A61B 8/00* (2006.01)
*A61B 8/08* (2006.01)

(52) U.S. Cl.
CPC ................ *A61B 1/018* (2013.01); *A61B 1/05* (2013.01); *A61B 8/12* (2013.01); *A61B 1/00043* (2013.01); *A61B 1/00096* (2013.01); *A61B 8/08* (2013.01); *A61B 8/467* (2013.01)

(58) Field of Classification Search
USPC ..................................................... 264/342 R
See application file for complete search history.

(56) References Cited

U.S. PATENT DOCUMENTS

| | | | |
|---|---|---|---|
| 2008/0119738 A1 | 5/2008 | Imahashi et al. | |
| 2013/0303853 A1* | 11/2013 | Takahashi | A61B 1/0051 600/134 |
| 2014/0039258 A1* | 2/2014 | Sekiguchi | A61B 5/062 600/117 |
| 2014/0243595 A1* | 8/2014 | Endo | A61B 1/00124 600/110 |
| 2015/0230692 A1 | 8/2015 | Matsuda et al. | |
| 2015/0265137 A1 | 9/2015 | Takahashi | |

FOREIGN PATENT DOCUMENTS

| | | |
|---|---|---|
| JP | H10108049 A | 4/1998 |
| JP | 2005342129 A | 12/2005 |
| JP | 2006212353 A | 8/2006 |

OTHER PUBLICATIONS

Japanese Decision to Grant a Patent dated Jun. 1, 2017 issued in JP 2017-526004.

Chinese Office Action dated Sep. 27, 2019 in Chinese Patent Application No. 201680020278.2.

* cited by examiner

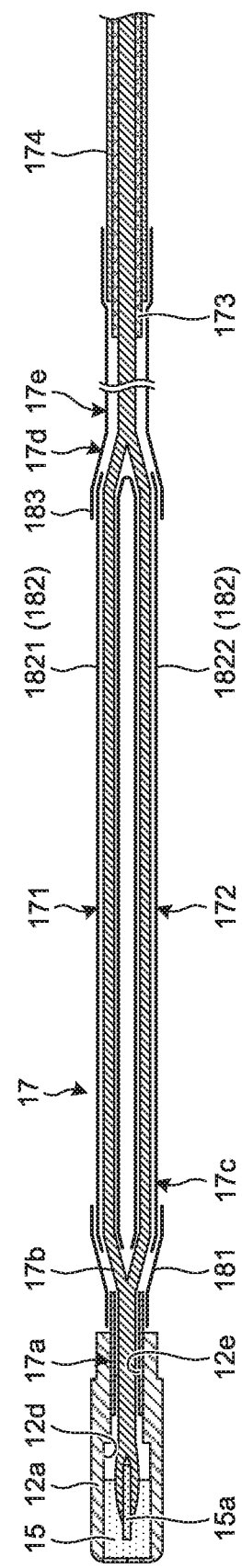

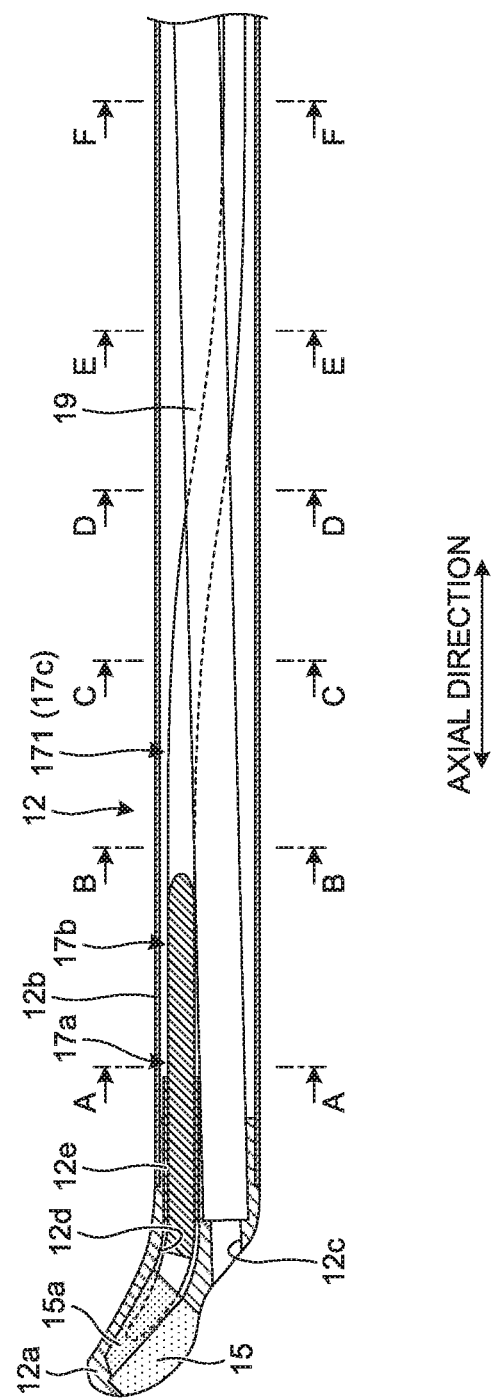

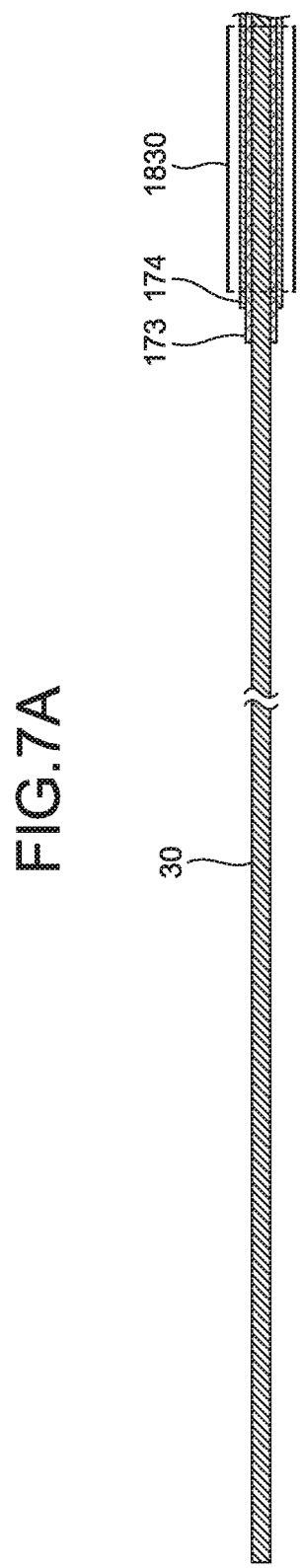

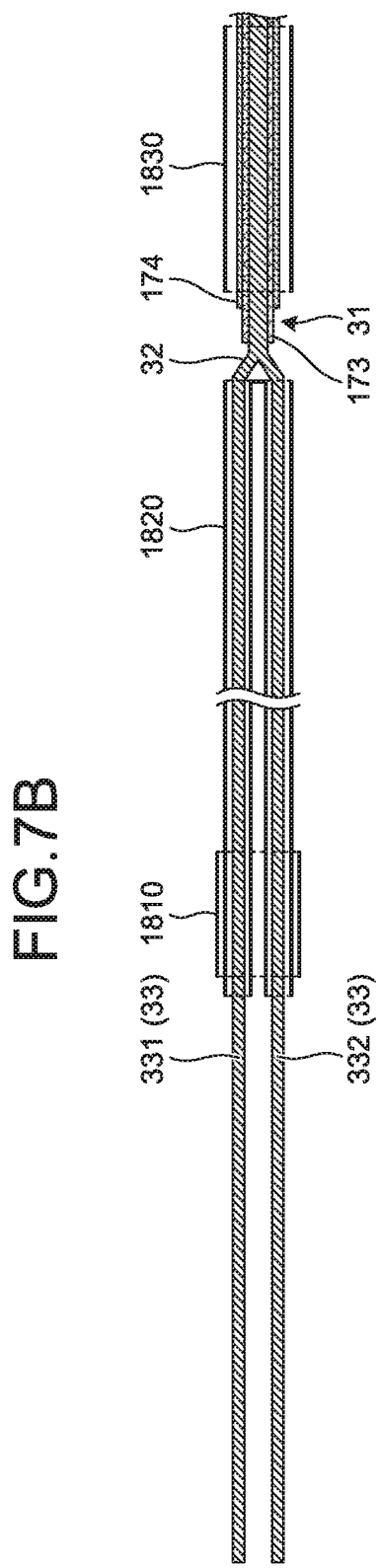

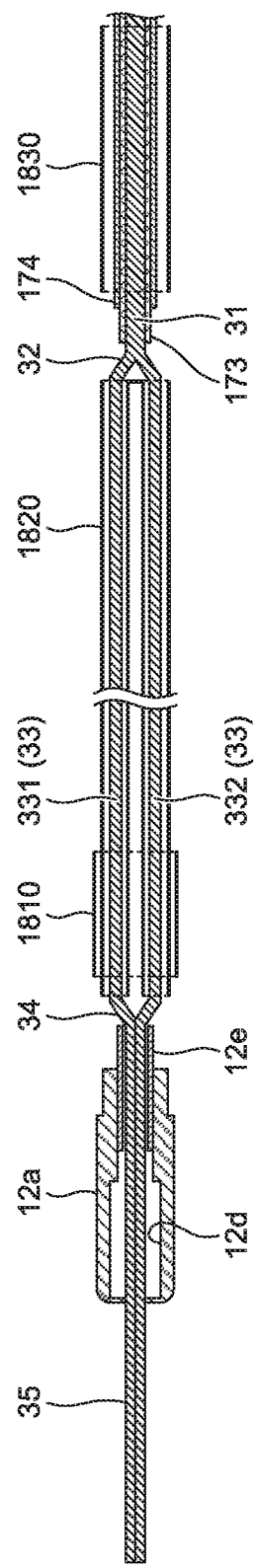

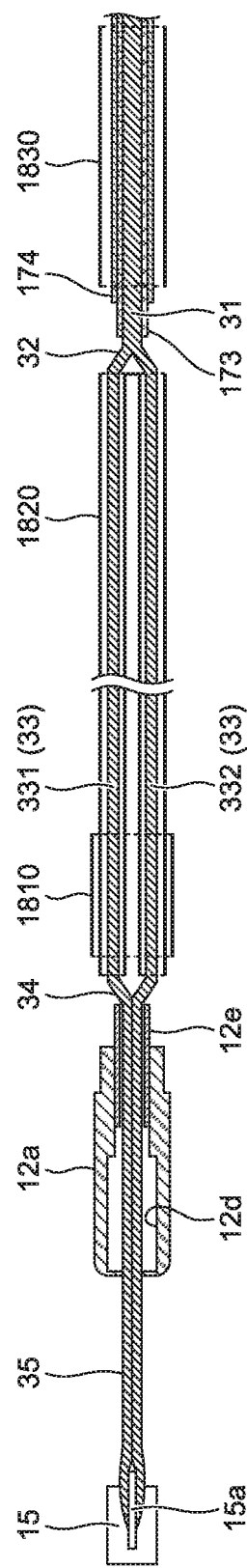

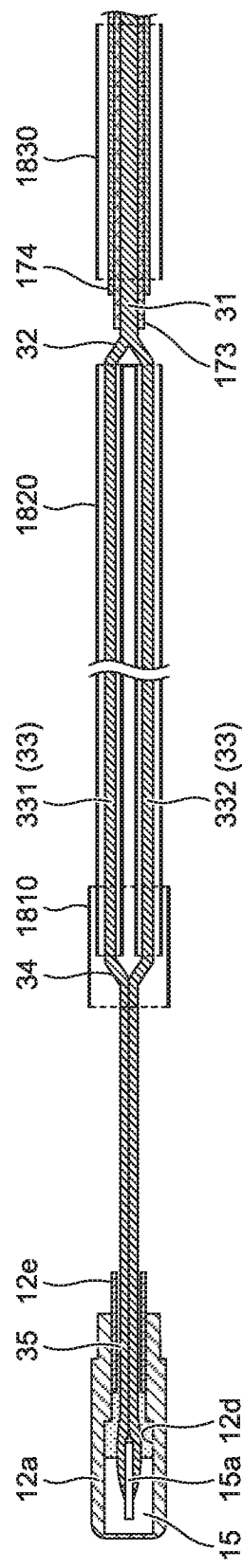

METHOD OF MANUFACTURING ENDOSCOPE AND ENDOSCOPE

CROSS-REFERENCE TO RELATED APPLICATIONS

This application is a continuation of PCT international application Ser. No. PCT/JP2016/085634 filed on Nov. 30, 2016 which designates the United States, incorporated herein by reference, and which claims the benefit of priority from Japanese Patent Application No. 2016-018919, filed on Feb. 3, 2016, incorporated herein by reference.

BACKGROUND

1. Technical Field

The disclosure relates to a method of manufacturing an endoscope and the endoscope.

2. Related Art

In the related art, a rigid or flexible endoscope is used at the time of observing an organ of a subject such as a patient and a material. For example, an operator such as a doctor uses an endoscope provided with an ultrasound transducer that transmits and receives ultrasound to and from a distal end of an insertion portion, and performs observation of an observation target according to information on a property of the observation target generated based on an ultrasound echo received from the ultrasound transducer.

The ultrasound transducer includes a plurality of piezoelectric elements each of which converts an electrical pulse signal into an ultrasound pulse (acoustic pulse) and emits the converted signal to the observation target, and further, converts the ultrasound echo reflected by the observation target into an electrical echo signal and outputs the converted signal. Each piezoelectric element is electrically connected to the ultrasound observation apparatus via a plurality of cables.

A treatment tool channel into which a treatment tool or the like is inserted to extend from the distal end of the insertion portion is provided in the insertion portion of the endoscope. In the case of the rigid endoscope, the treatment tool channel is a cylindrical member having rigidity and is provided from the distal end of the insertion portion to a proximal end side.

Meanwhile, arrangement of internals having rigidity, such as the treatment tool channel, is sometimes changed in the inside of the insertion portion of the rigid endoscope. At this time, there is a case where the treatment tool channel and a cable interfere with each other so that it is difficult to change the arrangement of the internals. As a technique for such a change of arrangement of internals, there is known a technique in which some of a plurality of signal lines in a cable are divided into a plurality of bundles to avoid interference with the internals (for example, see JP 2005-342129 A). According to the technique disclosed in JP 2005-342129 A, it is possible to change the arrangement of internals by avoiding the interference between the internals and the cable.

SUMMARY

In some embodiments, a method of manufacturing an endoscope provided with an insertion portion to be inserted into a subject is provided, the insertion portion having a distal end provided with an image sensor, the insertion portion into which a cylindrical channel and a signal cable are inserted, the cylindrical channel into which an elongated member is insertable, the signal cable being configured to be electrically connected to the image sensor. The method includes: dividing some of a plurality of signal lines to transmit a signal acquired by the image sensor into a plurality of bundle portions; notching a part of a tube having heat shrinkability and an insulation property excluding a part in a circumferential direction of the tube to form one or a plurality of notch portions; cutting at least one end portion of the tube in a state where the tube is folded with each notch portion as a base point to produce a first heat-shrinkable tube having a plurality of cylindrical portions with aligned end portions in longitudinal directions of the cylindrical portions; inserting the divided bundle portions into the plurality of cylindrical portions of the first heat-shrinkable tube, respectively; inserting the signal lines into a second heat-shrinkable tube, different from the first heat-shrinkable tube, the second heat-shrinkable tube having heat shrinkability and an insulation property; heating at least an overlapping portion in a state where the first and second heat-shrinkable tubes partially overlap each other to cause heat shrinkage; inserting the signal cable and the channel into a tubular portion having a tubular shape into which the signal cable and the channel are insertable; and connecting the tubular portion to a distal end constituting portion where the image sensor is held to form the insertion portion.

In some embodiments, an endoscope provided with an insertion portion to be inserted into a subject is provided. The endoscope includes: an image sensor configured to sequentially acquire images of the subject; a distal end constituting portion provided at a distal end of the insertion portion and configured to hold the image sensor; a signal cable including first and second cable portions which include a plurality of signal lines extending from the image sensor and configured to transmit the signals acquired by the image sensor, the first cable portion being connected to the image sensor and where the signal lines extend from the image sensor in a bundle, the second cable portion extending from an end portion of the first cable portion on an opposite side to a side connected to the image sensor and including a plurality of bundle portions formed by dividing the plurality of signal lines into a plurality of bundles; a cylindrical channel which is provided inside the insertion portion and into which an elongated member is insertable; and a tubular portion having a tubular shape into which the signal cable and the channel are insertable. The signal cable is provided with: an insulating first tube configured to cover the plurality of signal lines of the first cable portion; and an insulating second tube including a plurality of cylindrical portions where at least one ends of adjacent cylindrical portions are connected to each other, the cylindrical portions being configured to cover the plurality of bundle portions, respectively, and having same lengths in longitudinal directions of the cylindrical portions. A part of the first tube is in close contact with a part of the second tube.

The above and other features, advantages and technical and industrial significance of this disclosure will be better understood by reading the following detailed description of presently preferred embodiments of the disclosure, when considered in connection with the accompanying drawings.

BRIEF DESCRIPTION OF THE DRAWINGS

FIG. 3 is a cross-sectional view schematically illustrating a configuration of a main part of the rigid endoscope body of the rigid endoscopic system according to the first embodiment of the disclosure;

FIG. 4 is a cross-sectional view schematically illustrating a distal end configuration of the rigid endoscope body of the rigid endoscopic system according to the first embodiment of the disclosure;

FIG. 7A is a view for describing a method of manufacturing a signal cable in the rigid endoscope body according to the first embodiment of the disclosure;

FIG. 7B is a view for describing the method of manufacturing the signal cable in the rigid endoscope body according to the first embodiment of the disclosure;

FIG. 7C is a view for describing the method of manufacturing the signal cable in the rigid endoscope body according to the first embodiment of the disclosure;

FIG. 7D is a view for describing the method of manufacturing the signal cable in the rigid endoscope body according to the first embodiment of the disclosure;

FIG. 7E is a view for describing the method of manufacturing the signal cable in the rigid endoscope body according to the first embodiment of the disclosure;

DETAILED DESCRIPTION

Hereinafter, modes (hereinafter, embodiments) for carrying out the present invention will be described with reference to the drawings. Incidentally, the disclosure is not limited to the embodiments to be described below. In addition, the same parts are denoted by the same reference signs when the drawings are described.

First Embodiment

Figure 1:
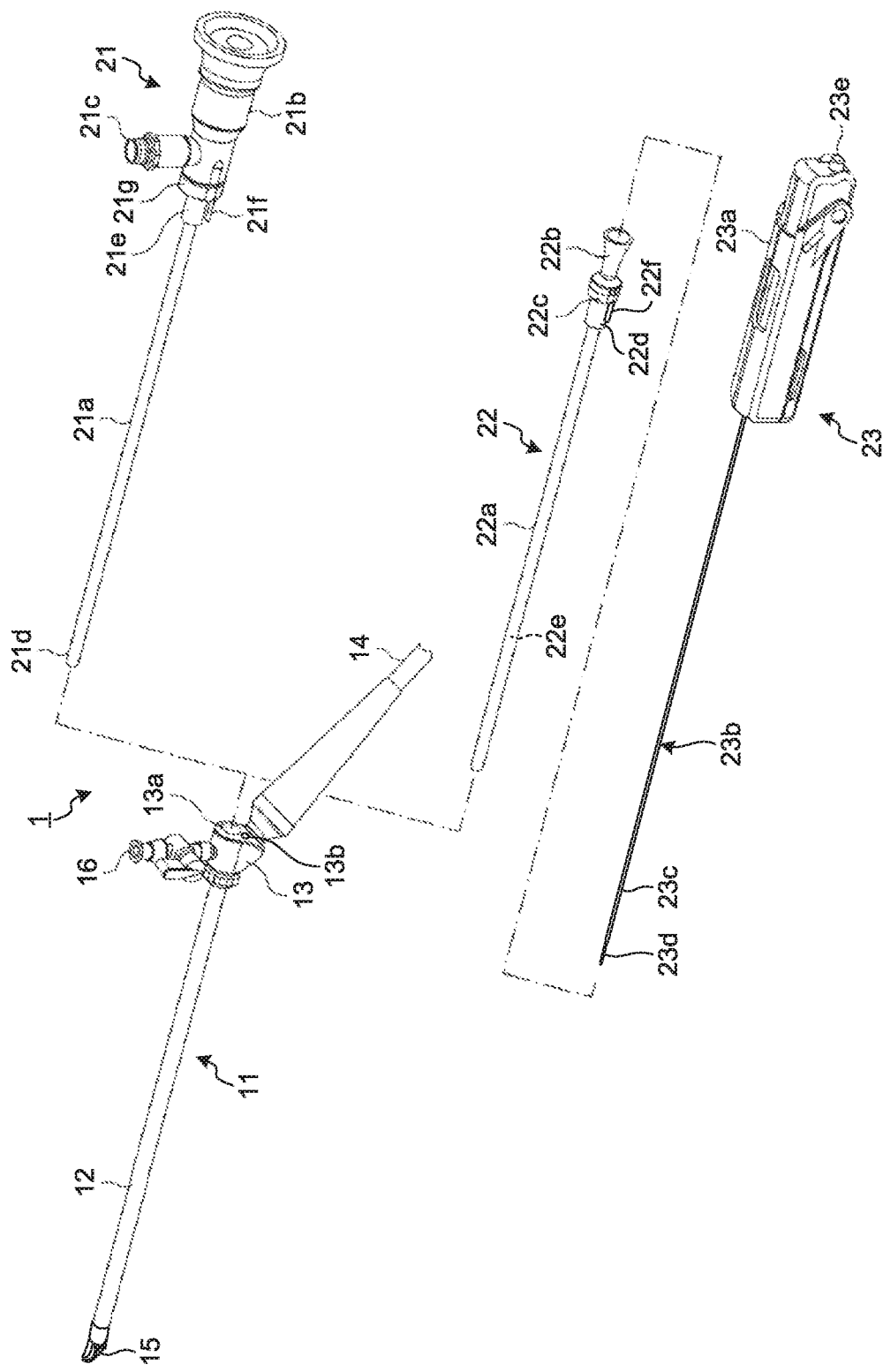
FIG. 1 is a perspective view schematically illustrating a rigid endoscopic system according to a first embodiment of the disclosure.
Figure 2:
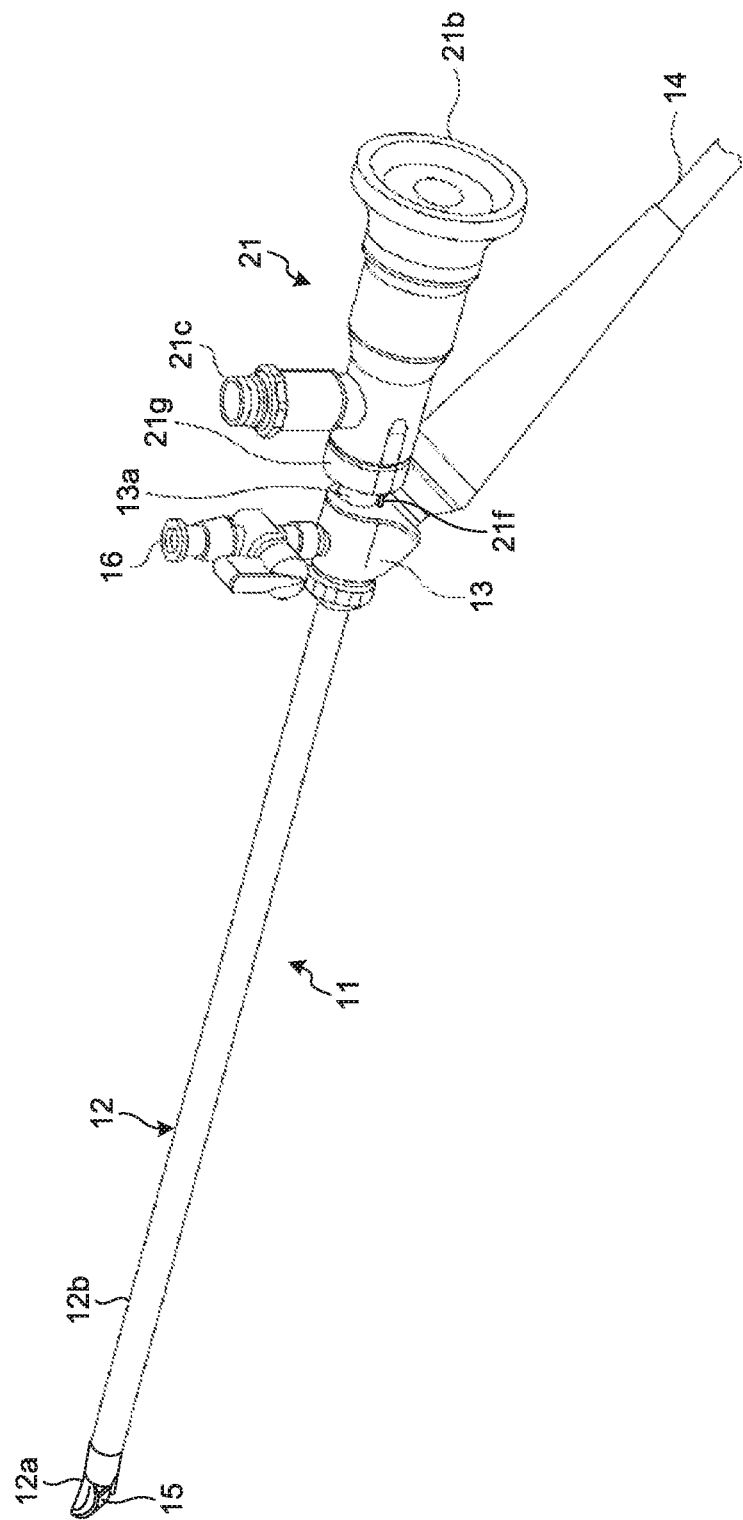
FIG. 2 is a perspective view schematically illustrating a configuration in a case where an optical viewing tube is attached to a rigid endoscope body of the rigid endoscopic system according to the first embodiment of the disclosure.

FIG. 1 is a perspective view schematically illustrating a rigid endoscopic system according to a first embodiment of the disclosure. FIG. 2 is a perspective view schematically illustrating a configuration in a case where an optical viewing tube is attached to a rigid endoscope body of the rigid endoscopic system according to the first embodiment. FIG. 3 is a cross-sectional view schematically illustrating a configuration of a main part of the rigid endoscope body of the rigid endoscopic system according to the first embodiment, and is the cross-sectional view illustrating a configuration in a case where the rigid endoscopic system is stretched linearly. FIG. 4 is a cross-sectional view schematically illustrating a distal end configuration of the rigid endoscope body of the rigid endoscopic system according to the first embodiment.

A rigid endoscopic system 1 is a system that performs ultrasound diagnosis inside a subject, such as a human, using an ultrasound endoscope, and, for example, is used at the time of transurethral sampling of a living tissue of the prostate. The rigid endoscopic system 1 includes a rigid endoscope body 11, an optical viewing tube 21 as an imaging device, a treatment tool guide 22, and a treatment tool device 23.

The rigid endoscope body 11 has a first insertion portion 12 to be inserted into a lumen (for example, a urethra) of the subject, a grip portion 13 is provided on a font side of the first insertion portion 12, and a universal cord 14 extends from an opposite side to a side of the grip portion 13 that is connected to the first insertion portion 12. FIG. 2 illustrates the configuration in a case where the optical viewing tube 21 is attached to the rigid endoscope body 11 as an example of use modes of the rigid endoscopic system 1.

The first insertion portion 12 is rigid and linearly extends, and a signal cable 17 extending from the universal cord 14 is inserted through a lower side of the inside thereof along an axial direction. The first insertion portion 12 includes a distal end constituting portion 12a, which is provided at a distal end of the first insertion portion 12 and holds an ultrasound transducer 15 configured to acquire information on the subject, and a tubular portion 12b having a tubular shape whose distal end is fitted to a proximal end side of the distal end constituting portion 12a and whose proximal end is connected to the grip portion 13 (see FIG. 4). In addition, a communication hole 12c communicating with a first channel 19 to be described later and a mounting portion 12d to mount the ultrasound transducer 15 are formed in the distal end constituting portion 12a. An insulating pipe 12e through which the signal cable 17 is insertable is provided in the mounting portion 12d.

In addition, the ultrasound transducer 15, which is an image sensor configured to acquire the information on the subject, is provided at the distal end of the first insertion portion 12. The ultrasound transducer 15 is configured using, for example, a convex array ultrasound transducer, and a distal end portion of the signal cable 17 is connected thereto. The ultrasound transducer 15 has a plurality of piezoelectric elements arranged along an axial core of the first insertion portion 12 and arranged to perform a fan-like scan on extension of a central axis of the first insertion portion 12. The ultrasound transducer 15 uses an ultrasound transducer provided at a distal end portion thereof to convert an electric pulse signal received from a control device, for example, a signal processing unit to be described later, into an ultrasound pulse (acoustic pulse) and emit the converted signal to the subject, and to convert an ultrasound echo reflected by the subject into an electrical echo signal expressed in a voltage change and output the converted echo signal.

Incidentally, the ultrasound transducer 15 may be any of a convex transducer and a linear transducer. In the first embodiment, the description is given assuming that the ultrasound transducer 15 is the convex ultrasound transducer that electronically performs the scan by providing the plurality of piezoelectric elements in an array and electronically switching the piezoelectric elements involved in transmission and reception.

Although not illustrated, a connector is provided at a proximal end of the universal cord 14, and the connector is connected to the signal processing unit. The signal processing unit transmits a drive signal to the ultrasound transducer 15 via the signal cable 17, processes an ultrasound signal received by the ultrasound transducer 15 to generate an ultrasonic tomographic image of a tissue present in a depth direction more than a body cavity wall of the subject, and displays the ultrasound tomographic image on a monitor (not illustrated).

In addition, a water supply port 16 with a cock is provided at an upper part of the grip portion 13. The water supply port 16 communicates with the first channel 19 to be described later, and enables a perfusate to be freely supplied via a perfusion tube (not illustrated). An operator can appropriately supply the perfusate into the first channel 19 by opening the cock of the water supply port 16.

The first channel 19 is provided inside the first insertion portion 12 so as to be inclined with respect to the axial direction of the first insertion portion 12. Specifically, a distal end portion of the first channel 19 is opened at a distal end surface of the first insertion portion 12 on the opposite side to the grip portion 13 side, and a proximal end portion thereof is opened at a proximal end surface of the first insertion portion 12 on the grip portion 13 side. The proximal end portion of the first channel 19 is positioned on the water supply port 16 side in a radial direction of the first insertion portion 12 and the distal end portion thereof is positioned on the opposite side to the water supply port 16 side in the radial direction of the first insertion portion 12. The first channel 19 is a cylindrical member having rigidity that is formed using, for example, stainless steel or the like. A wall thickness of the first channel 19 is preferably 0.15 mm to 0.20 mm in terms of reducing an outer diameter of the first insertion portion 12. Incidentally, the description is given in the present specification assuming that a straight line, which passes through each center of an aperture of the distal end surface on the opposite side to the grip portion 13 side of the first insertion portion 12 and an aperture of the proximal end surface on the grip portion 13 side of the first insertion portion 12, is inclined with respect to a longitudinal axis of the tubular portion 12b.

In addition, an insertion guide hole 13a whose distal end communicates with the first channel 19 and whose proximal end is opened to the proximal end surface of the grip portion 13 is formed in the grip portion 13. Here, a positioning hole 13b is drilled in the proximal end surface of the grip portion 13 to be engaged with positioning pins protruding from the optical viewing tube 21 and the treatment tool guide 22. Incidentally, the retention may be performed using a fixing screw that fixes the positioning pin to the grip portion 13.

In addition, a second insertion portion 21a provided in the optical viewing tube 21 and a third insertion portion 22a provided in the treatment tool guide 22 are selectively inserted and removed into and from the first channel 19 of the rigid endoscope body 11. Both the insertion portions 21a and 22a are rigid and extend linearly, and an inner diameter of the first channel 19 is set to a size to be compatible to an outer diameter of the second insertion portion 21a. On the other hand, an outer diameter of the third insertion portion 22a is set to be equal to the outer diameter of the second insertion portion 21a. In addition, a minute gap that enables circulation of the perfusate is secured between an inner periphery of the first channel 19 and each outer periphery of the insertion portions 21a and 22a. Therefore, the inner diameter of the first channel 19 is set to be slightly larger than the outer diameter of both the insertion portions 21a and 22a by the gap causing the circulation of the perfusate.

In addition, as illustrated in FIG. 1, an eyepiece portion 21b is provided on a front side of the second insertion portion 21a provided in the optical viewing tube 21, and a mouthpiece portion 21c into which a light guide (not illustrated) is inserted is provided at an upper part in the vicinity of a distal end of the eyepiece portion 21b. The light guide passes through the inside of the second insertion portion 21a and extends to a distal end direction, and illumination light transmitted through the light guide is emitted from an illumination window (not illustrated) provided at the distal end portion of the second insertion portion 21a and the body cavity wall of the subject is irradiated with the illumination light. In addition, an observation window 21d is provided at the distal end of the second insertion portion 21a to be adjacent to the illumination window, reflection light from the body cavity wall of the subject is incident on the observation window 21d, and an object image formed on an optical member, such as an objective lens, provided inside the observation window 21d is transmitted to the eyepiece portion 21b through a relay optical system and is observed.

Further, a flange portion 21g is formed at the distal end of the eyepiece portion 21b. A support portion 21e protrudes from a center of a distal end surface of the flange portion 21g. In addition, the proximal end portion of the second insertion portion 21a is supported by the support portion 21e. The distal end surface of the flange portion 21g faces the proximal end surface of the grip portion 13 when the second insertion portion 21a is inserted into the rigid endoscope body 11 via the insertion guide hole 13a. At this time, the support portion 21e is inserted through the insertion guide hole 13a. In addition, a positioning pin 21f protrudes from a lower part of the distal end surface of the flange portion 21g. The positioning pin 21f is engaged with the positioning hole 13b having an aperture at the proximal end surface of the grip portion 13, thereby restricting movement in a rotation direction.

The treatment tool guide 22 has a third insertion portion 22a, an inducing portion 22b, a flange portion 22c, and a support portion 22d. The inducing portion 22b is provided on a front side of the third insertion portion 22a and has a funnel shape. Further, the flange portion 22c is formed at a distal end of the inducing portion 22b, the support portion 22d protrudes from the center of the distal end surface of the inducing portion 22b, and a proximal end of the third insertion portion 22a is supported by the support portion 22d. A distal end surface of the flange portion 22c faces the proximal end surface of the grip portion 13 when the third insertion portion 22a is inserted into the rigid endoscope body 11 via the insertion guide hole 13a. At this time, the support portion 22d is inserted through the insertion guide hole 13a. In addition, a positioning pin 22f protrudes from a lower part of the distal end surface of the flange portion 22c. The positioning pin 22f is engaged with the positioning hole 13b having an aperture at the proximal end surface of the grip portion 13, thereby restricting movement in a rotation direction.

A second channel 22e whose distal end has an aperture at a distal end surface of the third insertion portion 22a and whose proximal end communicates with an inducing hole formed at the inducing portion 22b is formed inside the third insertion portion 22a. An elongated and rigid treatment tool 23b, which linearly extends forward from a device main body 23a and is provided in the treatment tool device 23, can be inserted and removed into and from the second channel 22e.

The second channel 22e functions as a guide at the time of inserting and removing the treatment tool 23b, and an inner diameter of the second channel 22e is formed to be slightly larger than an outer diameter of the treatment tool 23b. Incidentally, the third insertion portion 22a is formed using a pipe material, the inside thereof is filled with a resin material, and the second channel 22e is formed in this filling resin material, in the first embodiment. Incidentally, the second channel 22e may be formed by forming a hole in the third insertion portion 22a made of a solid metallic material.

In the first embodiment, a biopsy device is illustrated as an example of the treatment tool device 23, and a needle portion of the biopsy device corresponds to the treatment tool 23b. Therefore, a description will be given by replacing the treatment tool device 23 with a biopsy device 23 and the treatment tool 23b with a needle portion 23b, hereinafter.

The needle portion 23b has a guide tube needle 23c having a smaller outer diameter than the second insertion portion 21a of the optical viewing tube 21 and a biopsy needle 23d, and the biopsy needle 23d is inserted through the guide tube needle 23c so as to freely advance and retreat. In addition, a pocket is formed on a distal end side of the biopsy needle 23d. When a launch button 23e provided on the back of the device main body 23a is pressed, the biopsy needle 23d protrudes forward by receiving a resilient force of a spring built in the device main body 23a, is punctured into the tissue of the subject, and the biopsy tissue is taken into the pocket. When the launch button 23e is pressed, the guide tube needle 23c protrudes continuously to the biopsy needle 23d. The biopsy tissue is cut out and taken into the pocket when a distal end of the guide tube needle 23c passes over the pocket.

The first channel 19 is arranged at a position protruding to a scan plane (observation visual field) of the ultrasound transducer 15. Thus, when the needle portion 23b is configured to protrude forward from the first channel 19, the needle portion 23b passes through the scan plane of the ultrasound transducer 15, and accordingly, it is possible to display the needle portion 23b in the ultrasound tomographic image on the monitor.

The needle portion 23b of the present embodiment is inserted through the first channel 19 via the third insertion portion 22a provided in the treatment tool guide 22. Therefore, when the outer diameter of the third insertion portion 22a is set to correspond to the inner diameter of the first channel 19, and the inner diameter of the second channel 22e formed in the third insertion portion 22a is set to correspond to the outer diameter of the needle portion 23b, it is possible to accurately cause the needle portion 23b, narrower than the second insertion portion 21a of the optical viewing tube 21, to protrude on the scan plane of the ultrasound transducer 15.

Figure 5A:
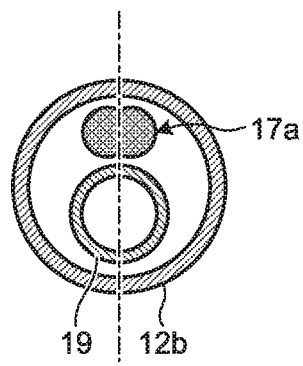
FIG. 5A is a cross-sectional view of the rigid endoscope body corresponding to line A-A illustrated in FIG. 4.
Figure 5B:
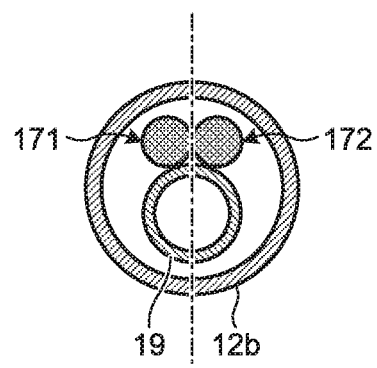
FIG. 5B is a cross-sectional view of the rigid endoscope body corresponding to line B-B illustrated in FIG. 4.
Figure 5C:
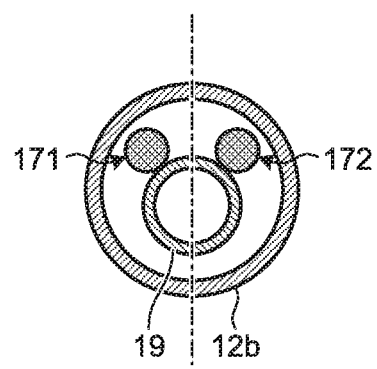
FIG. 5C is a cross-sectional view of the rigid endoscope body corresponding to line C-C illustrated in FIG. 4.
Figure 5D:
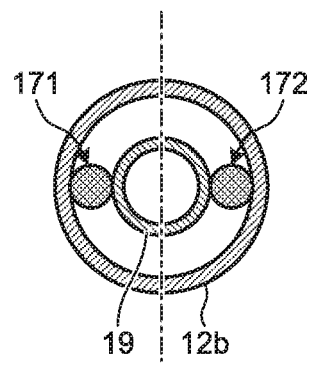
FIG. 5D is a cross-sectional view of the rigid endoscope body corresponding to line D-D illustrated in FIG. 4.
Figure 5E:
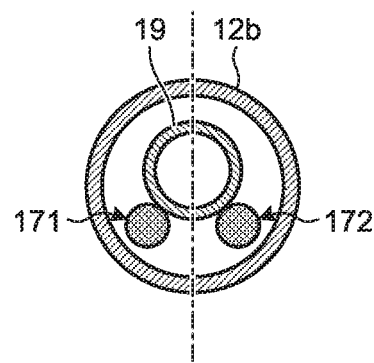
FIG. 5E is a cross-sectional view of the rigid endoscope body corresponding to line E-E illustrated in FIG. 4.
Figure 5F:
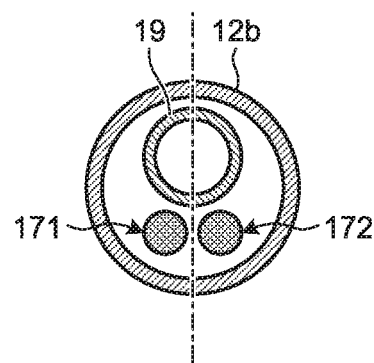
FIG. 5F is a cross-sectional view of the rigid endoscope body corresponding to line F-F illustrated in FIG. 4.

Subsequently, an internal configuration of the rigid endoscope body 11 will be described with reference to FIGS. 3, 4 and 5A to 5F. FIG. 5A is a cross-sectional view of the rigid endoscope body corresponding to line A-A illustrated in FIG. 4. FIG. 5B is a cross-sectional view of the rigid endoscope body corresponding to line B-B illustrated in FIG. 4. FIG. 5C is a cross-sectional view of the rigid endoscope body corresponding to line C-C illustrated in FIG. 4. FIG. 5D is a cross-sectional view of the rigid endoscope body corresponding to line D-D illustrated in FIG. 4. FIG. 5E is a cross-sectional view of the rigid endoscope body corresponding to line E-E illustrated in FIG. 4. FIG. 5F is a cross-sectional view of the rigid endoscope body corresponding to line F-F illustrated in FIG. 4.

The signal cable 17 includes: a first cable portion 17a formed by bundling a plurality of signal lines connected to a relay board 15a electrically connected to each of the ultrasound transducer 15 and the signal cable 17; a branch portion 17b which is continuous to the first cable portion 17a and causes the plurality of signal lines to branch into two; a second cable portion 17c formed of two bundle portions (a first bundle portion 171 and a second bundle portion 172) branched by the branch portion 17b; a binding portion 17d that binds the first bundle portion 171 and the second bundle portion 172 into a bundle; and a third cable portion 17e which holds the bundle state and extends from the binding portion 17d to the grip portion 13 side, as illustrated in FIG. 3. In the third cable portion 17e, a comprehensive shield 173 is provided at an outer periphery of the plurality of signal lines, and a jacket 174 is provided at an outer periphery of the comprehensive shield 173. Incidentally, an end portion of the third cable portion 17e on the opposite side to the binding portion 17d is connected to a connector (not illustrated) which is electrically connected to the universal cord 14 via the grip portion 13.

Since the first channel 19 is provided so as to be inclined with respect to the axial direction of the first insertion portion 12 as described above, the signal cable 17 interferes with the first channel 19 when being provided so as to extend in parallel to the central axis of the first insertion portion 12. Thus, the signal cable 17 and the first channel 19 are arranged to cross each other while avoiding the interference therebetween by dividing some of the plurality of signal lines included in the signal cable 17 into two bundles and inserting the first channel 19 into a gap formed between the divided two bundles in the first embodiment (see FIG. 4).

Specifically, a bundle of the first cable portions 17a and the first channels 19 are arranged side by side in a vertical direction in the drawing from the ultrasound transducer 15 side of the first insertion portion 12 (see FIG. 5A). At this position, the first cable portion 17a is arranged on the ultrasound transducer 15 side, and the first channel 19 is arranged on the opposite side thereof.

As proceeding to the grip portion 13 side from the arrangement of FIG. 5A, the first bundle portion 171 and the second bundle portion 172 branched by the branch portion 17b move in directions opposite to each other along an outer periphery of the first channel 19 (see FIGS. 5B to 5F). At this time, the first channel 19 gradually moves in an upward direction in the drawing along the inclination. The arrangement of the signal cable 17 and the first channel 19 is opposite to the arrangement of FIG. 5A in front of the binding portion 17d. Thereafter, the signal lines of the first bundle portion 171 and the second bundle portion 172 are collected together by the binding portion 17d. In this manner, it is possible to change the arrangement of the signal cable 17 and the first channel 19 while avoiding the interference between the signal cable 17 and the first channel 19 by dividing the signal lines of the signal cable 17 into two without increasing a diameter of the tubular portion 12b.

In addition, the signal cable 17 is provided with a first tube 181, a second tube 182, and a third tube 183 (see FIG. 3). Each of the first tube 181, the second tube 182, and the third tube 183 is formed using a heat-shrinkable tube, and covers an outer periphery including a part of the signal cable 17, that is, at least a part of the signal cable 17 that is branched into two while including a region overlapping with each other between the adjacent tubes by heat shrinkage.

The first tube 181 covers a part of the first cable portion 17a including a part of the insulating pipe 12e, the branch portion 17b, and a part of the second cable portion 17c. The second tube 182 covers the first bundle portion 171 and the second bundle portion 172 and has one end covered by the first tube 181 and the other end covered by the third tube 183. The second tube 182 has two cylindrical portions (cylindrical portions 1821 and 1822) partially connected at one end side. The third tube 183 covers a part of the second cable portion 17c, the binding portion 17d, and a part of the third cable portion 17e.

Next, a manufacturing method of manufacturing the above-described rigid endoscope body 11 will be described with reference to FIGS. 6A to 6D and FIGS. 7A to 7E. FIGS. 6A to 6D are views for describing a method of producing the second tube according to the first embodiment. FIGS. 7A to 7E are views for describing a method of producing the signal cable in the rigid endoscope body according to the first embodiment. First, the manufacturing method (manufacturing step) of the second tube 182 will be described with reference to FIGS. 6A to 6D.

Figure 6A:
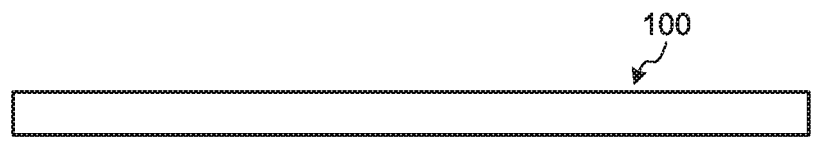
FIG. 6A is a view for describing a method of manufacturing a second tube according to the first embodiment of the disclosure.
Figure 6B:
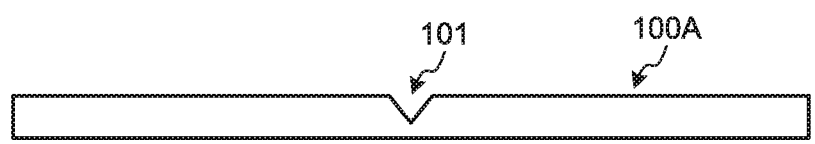
FIG. 6B is a view for describing the method of manufacturing the second tube according to the first embodiment of the disclosure.
Figure 6C:
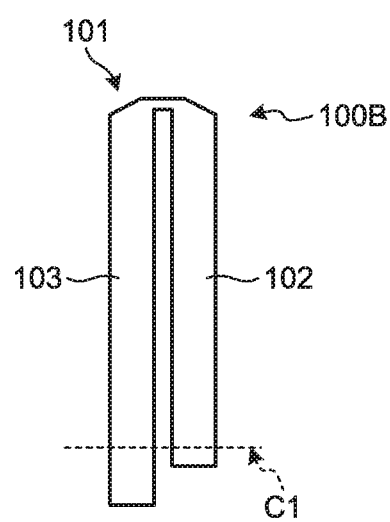
FIG. 6C is a view for describing the method of manufacturing the second tube according to the first embodiment of the disclosure.
Figure 6D:
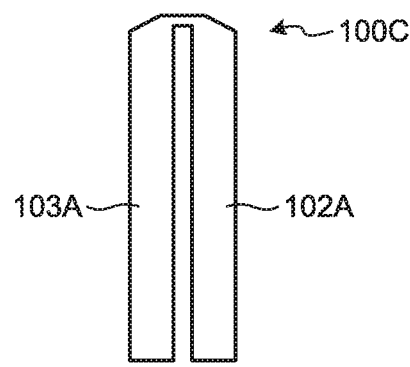
FIG. 6D is a view for describing the method of manufacturing the second tube according to the first embodiment of the disclosure.

First, a first molded body 100A in which a notch portion 101 is formed by forming a wedge-shaped cutout in a part of a center portion of an elastically deformable tube 100, as illustrated in FIG. 6A, is obtained (see FIG. 6B). Thereafter, the first molded body 100A is folded with the notch portion 101 as a base point such that the notch portion 101 is located outside, thereby obtaining a second molded body 100B in which a first cylindrical portion 102 and a second cylindrical portion 103 divided by the notch portion 101 are aligned along longitudinal directions thereof (see FIG. 6C). After producing the second molded body 100B, end portions of the first cylindrical portion 102 and the second cylindrical portion 103 on a side different from a connecting portion with the notch portion 101 are aligned with each other, the connecting portion connecting the first cylindrical portion 102 and the second cylindrical portion 103 to each other. Specifically, a part of each of the first cylindrical portion 102 and the second cylindrical portion 103 is cut along a cutting plane C1 illustrated in FIG. 6C. At this time, end portions of the first cylindrical portion 102 and the second cylindrical portion 103 on the notch portion 101 side are connected to each other, and thus, positions of the end portions on the side different from the connecting portion are aligned with each other. Accordingly, it is possible to align the positions of both ends of the first cylindrical portion 102 in the longitudinal direction with the positions of both ends of the second cylindrical portion 103 in the longitudinal direction and suppress deviation of a positional relationship therebetween, and it is possible to obtain a heat-shrinkable tube 100C including a first cylindrical portion 102A and a second cylindrical portion 103A, that is, the heat-shrinkable tube 100C (first heat-shrinkable tube) before heat shrinkage of the second tube 182 (see FIG. 6D).

Next, the manufacturing method of the signal cable 17 will be described with reference to FIGS. 7A to 7E. First, a third tube 1830 before heat shrinkage is inserted into a signal line group 30 configured of the plurality of signal lines, which is the signal cable 17 grouped in one bundle and provided with the comprehensive shield 173 and the jacket 174 on one end side, from the other end side to the jacket 174 (see FIG. 7A).

Thereafter, the plurality of signal lines are divided into two bundles to form a bifurcated portion 33 formed of a first bundle portion 331 and a second bundle portion 332 in a part of the signal line group 30 (see FIG. 7B, a division step). Accordingly, a signal line binding portion 32 and a first coaxial portion 31 corresponding to the binding portion 17d and the third cable portion 17e, respectively, described above are formed. After branching the signal line group 30, the above-described heat-shrinkable tube 100C (hereinafter, referred to as a second tube 1820) is inserted into the bifurcated portion 33 (a first insertion step). Specifically, the first bundle portion 331 is inserted into one cylindrical portion of the second tube 1820, for example, the first cylindrical portion 102A, and the second bundle portion 332 is inserted into the other cylindrical portion of the second tube 1820, for example, the second cylindrical portion 103A.

After inserting the second tube 1820 into the bifurcated portion 33, a first tube 1810 (a second heat-shrinkable tube) before heat shrinkage and the distal end constituting portion 12a are inserted into the plurality of signal lines (the signal line group 30) (a second insertion step). Thereafter, sides of the first bundle portion 331 and the second bundle portion 332, which are different from the signal line binding portion 32 side, are grouped to form a signal line branch portion 34 and a second coaxial portion 35 corresponding to the branch portion 17b and the first cable portion 17a, respectively (see FIG. 7C). At this time, the insulating pipe 12e is fitted in the mounting portion 12d of the distal end constituting portion 12a.

Thereafter, a plurality of signal lines of the second coaxial portion 35 and the relay board 15a are connected (FIG. 7D) to each other. At this time, the ultrasound transducer 15 may be connected in advance to the relay board 15a, or the ultrasound transducer 15 may be connected to the relay board 15a after connecting the plurality of signal lines and the relay board 15a to each other. After connecting the first cable portion 17a and the relay board 15a to each other, the ultrasound transducer 15 is accommodated in the distal end constituting portion 12a, and the ultrasound transducer 15 is attached and fixed to the distal end constituting portion 12a (see FIG. 7E, a first insertion portion forming step).

Thereafter, positions of the first tube 1810, the third tube 1830 and the signal lines are adjusted such that each of the first tube 1810 and the third tube 1830 covers a part of the second tube 1820, and the first tube 1810, the second tube 1820, and the third tube 1830 are heated to cause heat shrinkage so as to be crimped to the signal line (a heat shrinkage step). At this time, since the two cylindrical portions (the first cylindrical portion 102A and the second cylindrical portion 103A) of the second tube 1820 are connected to each other, it is possible to arrange the first cylindrical portion 102A and the second cylindrical portion 103A without misalignment only by adjusting the position of one of the two cylindrical portions even when both ends are covered with the first tube 1810 and the third tube 1830, respectively, and visual recognition thereof becomes difficult. Accordingly, it is possible to produce the above-described signal cable 17. Incidentally, a length of the overlapping portion where each of the first tube 1810 and the third tube 1830 covers a part of the second tube 1820, which is the length along the longitudinal direction of the tube, is preferably 4 mm or more. In addition, the first tube 1810 is heat-shrunk in the state of overlapping with a part of the insulating pipe 12e as understood from FIG. 3.

Thereafter, the first channel 19 is inserted into the gap formed by the first cylindrical portion 102A and the second cylindrical portion 103A (a third insertion step). Thereafter, the signal cable 17 and the first channel 19 are inserted into the tubular portion 12b, and the tubular portion 12b is mounted to the distal end constituting portion 12a, thereby forming the first insertion portion 12 into which the signal cable 17 and the first channel 19 are inserted (a second insertion portion forming step).

According to the first embodiment described above, it is configured such that the heat-shrinkable tube 100C, which is the second tube 182 before heat shrinkage, is produced by folding the first molded body 100A in which the notch portion 101 is formed by forming the wedge-shaped cutout in a part of the center portion of the elastically deformable tube 100 and aligning the end portions thereof, and the first bundle portion 331 and the second bundle portion 332 formed by branching a part of the signal line group 30 are inserted into the respective cylindrical portions of the heat-shrinkable tube 100C to be covered by heat shrinkage. Thus, it is possible to accurately arrange the second tube 182, which covers the respective bundle portions obtained by dividing some of the plurality of signal lines of the signal cable 17 inserted into the first insertion portion 12 into two bundles, without misalignment. Accordingly, it is possible to reliably secure insulation at the branch portion of the signal cable 17.

Incidentally, the order in the manufacturing method may be exchanged in the above-described first embodiment. For example, the first insertion portion forming step and the heat shrinkage step described above may be exchanged such that the connection between the relay board 15a and the signal line and the attaching and fixing of the ultrasound transducer 15 to the distal end constituting portion 12a are performed after causing heat shrinkage of the tube.

In addition, the description has been given in the above-described first embodiment regarding the case where the positions of the first tube 1810 and the third tube 1830 are adjusted, and the first tube 1810, the second tube 1820, and the third tube 1830 are heated to cause heat shrinkage so as to cover the signal cable 17. However, a region where the respective tubes overlap with each other, for example, a region where the first tube 1810 and the second tube 1820 overlap with each other and a region where the second tube 1820 and the third tube 1830 overlap with each other may be heated so that only the region where the respective tubes overlap with each other is heat-shrunk.

The description has been given in the above-described first embodiment regarding the case where the first molded body 100A in which the notch portion 101 is formed by forming the wedge-shaped cutout in a part of the center portion of the tube 100 is produced, but a cutout having another shape may be formed without being limited to the wedge shape.

First Modification of First Embodiment

Figure 8:
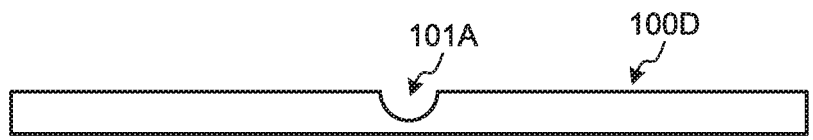
FIG. 8 is a view for describing a method of manufacturing a second tube according to a first modified example of the first embodiment of the disclosure.

FIG. 8 is a view for describing a method of manufacturing a second tube according to a first modified example of the first embodiment of the disclosure. In the first modified example, a notch portion 101A is formed by forming a semicircular cutout in a part of the center portion of the above-described tube 100 as illustrated in FIG. 8, thereby producing a first molded body 100D. Thereafter, a heat-shrinkable tube which is the second tube 182 before heat shrinkage is produced by folding the first molded body 100D and aligning end portions thereof.

Second Modification of First Embodiment

Figure 9:
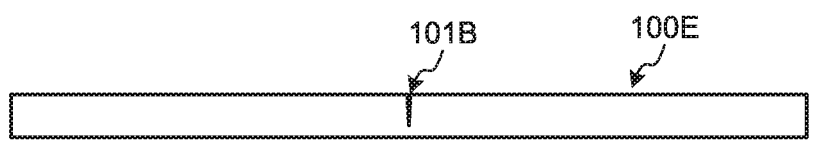
FIG. 9 is a view for describing a method for manufacturing a second tube according to a second modified example of the first embodiment of the disclosure.

FIG. 9 is a view for describing a method for manufacturing a second tube according to a second modified example of the first embodiment of the disclosure. In the second modified example, a notch portion 101B is formed by forming a linearly cutout (slit) in a part of the center portion of the above-described tube 100 as illustrated in FIG. 9, thereby producing a first molded body 100E. Thereafter, a heat-shrinkable tube which is the second tube 182 before heat shrinkage is produced by folding the first molded body 100E and aligning end portions thereof.

Third Modification of First Embodiment

In addition, a marker to instruct arrangement of the first tube 181 and the third tube 183 with respect to the second tube 182 may be provided in the second tube 182 (the second tube 1820 before heat shrinkage) according to the above-described first embodiment. Accordingly, it is possible to arrange the first tube 1810 and the third tube 1830 before heat shrinkage while confirming the positions thereof with respect to the second tube 1820 before heat shrinkage.

Figure 10:
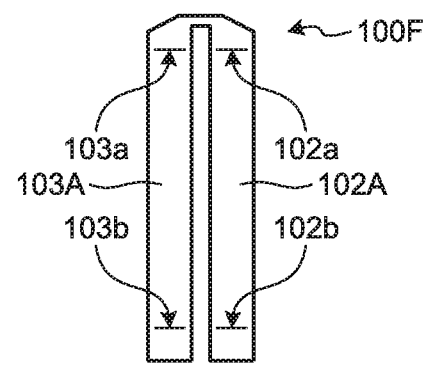
FIG. 10 is a view for describing a configuration of a second tube according to a third modified example of the first embodiment of the disclosure.

FIG. 10 is a view for describing a configuration of a second tube according to a third modified example of the first embodiment of the disclosure. In the third modified example, a description will be given regarding a configuration in which a plurality of markers (markers 102a, 102b, 103a and 103b) to instruct positions of the end portions of the first tube 181 and the third tube 183 are provided on a surface of a heat-shrinkable tube 100F, as an example of the marker to instruct the arrangement of the first tube 181 and the third tube 183 with respect to the second tube. The marker 102a instructs the position of the end portion of the third tube 183 (the third tube 1830) with respect to the first cylindrical portion 102A. The marker 103a instructs the position of the end portion of the third tube 183 with respect to the second cylindrical portion 103A. The marker 102b instructs the position of the end portion of the first tube 181 (the first tube 1810) with respect to the first cylindrical portion 102A. The marker 103b instructs the position of the end portion of the first tube 181 with respect to the second cylindrical portion 103A. Accordingly, when adjusting the positions of the first tube 1810 and the third tube 1830 as described with reference to FIG. 7E, it is possible to easily and reliably perform the adjustment.

Incidentally, the markers 102a, 102b, 103a and 103b may be provided by printing on the surface of the heat-shrinkable tube 100F or pasting a seal material or the like, or may be provided by forming a concave shape or a convex shape on the surface of the heat-shrinkable tube 100F.

Second Embodiment

Figure 11:
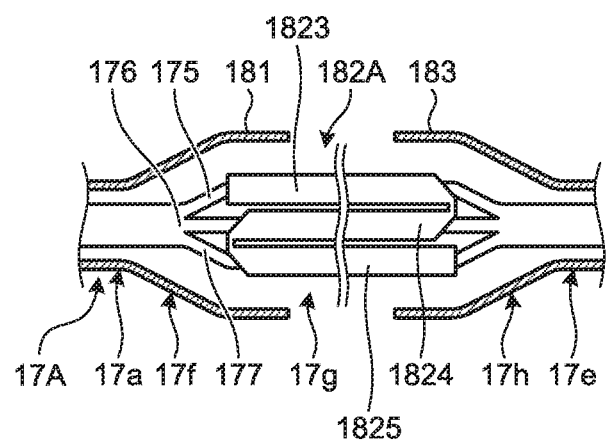
FIG. 11 is a partial cross-sectional view illustrating a configuration of a second tube according to a second embodiment of the disclosure.

Although the description has been given in the above-described first embodiment regarding the case where a part of the signal cable 17 is divided into two, a signal cable may be divided into a plurality of, that is three or more, bundles. In a second embodiment, an example in which a part of a signal cable 17A is divided into three will be described. FIG. 11 is a partial cross-sectional view illustrating a configuration of a second tube according to the second embodiment of the disclosure.

As illustrated in FIG. 11, the signal cable 17A according to the second embodiment includes: the above-described first cable portion 17a; a branch portion 17f which is continuous to the first cable portion 17a and branches a plurality of signal lines into three bundles; a second cable portion 17g formed of three bundle portions (a first bundle portion 175, a second bundle portion 176, and a third bundle portion 177) branched by the branch portion 17f; a binding portion 17h that binds the first bundle portion 175, the second bundle portion 176, and the third bundle portion 177 into a bundle; and the third cable portion 17e which holds the bundle state and extends from the binding portion 17h to the grip portion 13 side. Incidentally, the comprehensive shield 173 is provided at the outer periphery of the plurality of signal lines, and the jacket 174 is provided at the outer periphery of the comprehensive shield 173 in the third cable portion 17e, which is similar to the above-described first embodiment (see FIG. 3).

In addition, the signal cable 17A is provided with the above-described first tube 181 and third tube 183, and a second tube 182A. The second tube 182A is formed using a heat-shrinkable tube and covers a part of the plurality of signal lines including regions overlapping with the first tube 181 and the third tube 183, respectively, at both ends.

The first tube 181 covers a part of the first cable portion 17a and the branch portion 17f. The second tube 182A covers the first bundle portion 175, the second bundle portion 176, and the third bundle portion 177 and has one end covered by the first tube 181 and the other end covered by the third tube 183. The second tube 182A has three cylindrical portions (a first cylindrical portion 1823, a second cylindrical portion 1824, and a third cylindrical portion 1825) partially connected at one end side. The third tube 183 covers the binding portion 17h and a part of the third cable portion 17e.

Next, a manufacturing method of manufacturing the above-described second tube 182A will be described with reference to FIGS. 12A to 12D. FIGS. 12A to 12D are views for describing the method of producing the second tube according to the second embodiment.

Figure 12A:
FIG. 12A is a view for describing a method of manufacturing the second tube according to the second embodiment of the disclosure.
Figure 12B:
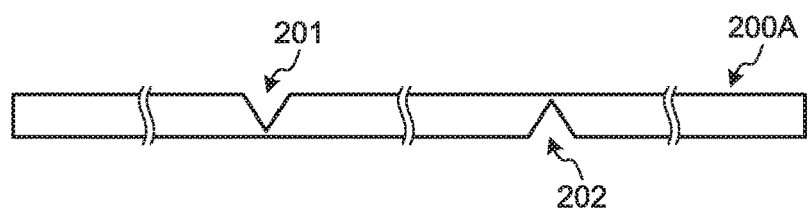
FIG. 12B is a view for describing the method of manufacturing the second tube according to the second embodiment of the disclosure.

First, two wedge-shaped cutouts are formed in a part of an elastically deformable tube 200 as illustrated in FIG. 12A, thereby obtaining a first molded body 200A in which two notch portions (a first notch portion 201 and a second notch portion 202) are formed (FIG. 12B). The first notch portion 201 and the second notch portion 202 are provided on sides facing each other.

In addition, the first notch portion 201 and the second notch portion 202 are provided at positions that satisfy the following conditions 1 to 3.

1) The first notch portion 201 and the second notch portion 202 are provided at a position at which a length therebetween is equal to a length in a longitudinal direction of the above-described second cylindrical portion 1824.
2) The first notch portion 201 is provided at a position at which a length from an end portion of the tube 200 on the first notch portion 201 side to a center position of the first notch portion 201 is equal to or longer than a length in the longitudinal direction of the above-described first cylindrical portion 1823.
3) The second notch portion 202 is provided at a position at which a length from an end portion of the tube 200 on the second notch portion 202 side to a center position of the second notch portion 202 is equal to or longer than a length in the longitudinal direction of the above-described third cylindrical portion 1825.

Incidentally, the above-described length relationship relates to each length at the time of heat shrinkage, and the first notch portion 201 and the second notch portion 202 are provided at a position on consideration of shrinkage caused by heat shrinkage with respect to the tube 200 before heat shrinkage.

Figure 12C:
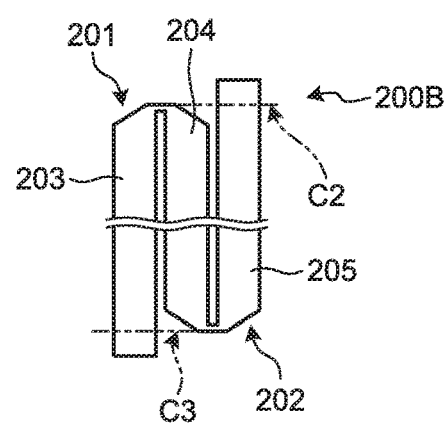
FIG. 12C is a view for describing the method of manufacturing the second tube according to the second embodiment of the disclosure.
Figure 12D:
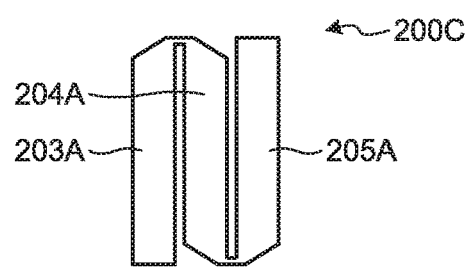
FIG. 12D is a view for describing the method of manufacturing the second tube according to the second embodiment of the disclosure.

Thereafter, the first molded body 200A is folded in an S shape such that each of the first notch portion 201 and the second notch portion 202 is located outside, thereby obtaining a second molded body 200B aligned in the longitudinal direction of three cylindrical portions (a first cylindrical portion 203, a second cylindrical portion 204, and a third cylindrical portion 205) divided by the first notch portion 201 and the second notch portion 202 (FIG. 12C).

After producing the second molded body 200B, end portions in the longitudinal direction of the three cylindrical portions are aligned. Specifically, a part of the third cylindrical portion 205 is cut along a cutting plane C2 that passes through end portions of the first cylindrical portion 203 and the second cylindrical portion 204 at a connecting portion on the first notch portion 201 side. On the other hand, a part of the first cylindrical portion 203 is cut along a cutting plane C3 that passes through end portions of the second cylindrical portion 204 and the third cylindrical portion 205 at a connecting portion on the second notch portion 202 side. Accordingly, it is possible to align the positions of both ends in the longitudinal direction and suppress deviation of a positional relationship therebetween, and it is possible to obtain a heat-shrinkable tube 200C including a first cylindrical portion 203A, a second cylindrical portion 204A, and a third cylindrical portion 205A, that is, the heat-shrinkable tube 200C (first heat-shrinkable tube) before heat shrinkage of the second tube 182A (see FIG. 12D).

When producing the signal cable 17A, the first channel 19 is inserted between the first cylindrical portion 203A and the second cylindrical portion 204A, and between the second cylindrical portion 204A and the third cylindrical portion 205A. Incidentally, the first channel 19 may be inserted into only one portion between the first cylindrical portion 203A and the second cylindrical portion 204A or between the second cylindrical portion 204A and the third cylindrical portion 205A.

According to the second embodiment described above, it is configured such that the heat-shrinkable tube 200C is produced by folding the first molded body 200A in which the first notch portion 201 and the second notch portion 202 are formed by forming the wedge-shaped cutouts from directions facing each other in a part of the elastically deformable tube 200 and aligning the end portions thereof, and the first bundle portion 175, the second bundle portion 176, and the third bundle portion 177 formed by branching some of the plurality of signal lines are inserted into the respective cylindrical portions of the heat-shrinkable tube 200C to be covered by heat shrinkage. Thus, it is possible to arrange the second tube 182A, which covers the respective bundle portions obtained by dividing some of the plurality of signal lines of the signal cable 17A inserted into the first insertion portion 12 into three bundles, without misalignment. Accordingly, it is possible to reliably secure insulation at the branch portion of the signal cable 17A.

The modes for carrying out the present invention have been described hereinbefore. However, the disclosure is not limited only to the embodiments and the modified examples described above. The disclosure is not limited to the embodiments and the modified example described above, but may include various embodiments within a range that does not depart from the technical ideas described in the claims. In addition, each configuration of the embodiments and the modified examples may be appropriately combined.

In addition, the description has been given in the above-described first and second embodiments assuming that the plurality of signal lines are bundled together again by the binding portion 17d or 17h, but the two bundles (the first bundle portion 171 and the second bundle portion 172) or the three bundles (the first bundle portion 175, the second bundle portion 176, and the third bundle portion 177) may be directly connected to the connector. In this case, the heat-shrinkable tube covering the signal line is configured only of the first tube 181 and the second tube 182 or 182A.

In addition, the description has been given in the above-described first and second embodiments by exemplifying the piezoelectric element as the part that emits ultrasound and converts the ultrasound incident from the outside into the echo signal, but the disclosure is not limited thereto, and an element manufactured in micro electro mechanical systems (MEMS), for example, capacitive micromachined ultrasound transducers (C-MUT) may be used.

In addition, the description has been given in the above-described first and second embodiments by exemplifying the ultrasound endoscope (ultrasound miniature probe) that observes the inside of the subject via the urethra, but a device that is inserted into a biliary tract, a bile duct, a pancreatic duct, a trachea, a bronchus, a ureter other than the urethra and observes surrounding organs (a pancreas, lungs, a bladder, lymph nodes, and the like) thereof.

In addition, the description has been given in the above-described first and second embodiments by exemplifying the ultrasound endoscope, but the disclosure is not limited thereto as long as being an endoscope that includes a signal cable to transmit an image signal. For example, the disclosure can be applied to an oral endoscope which is inserted into a digestive tract (an esophagus, a stomach, a duodenum, or a large intestine) or the respiratory organ (a trachea or a bronchial tube) of the subject to capture digestive tracts and respiratory organs, that is, the oral endoscope provided with a flexible insertion portion that includes an image sensor as an image sensor. In particular, the disclosure is advantageous in an endoscope provided with an image sensor that includes a cable having a lot of signal lines and requiring insulation treatment, such as a charge coupled device (CCD) used for a high-speed camera.

According to some embodiments, there is an effect that it is possible to accurately arrange the insulating tube to cover the signal lines divided into the plurality of bundles.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A method of manufacturing an endoscope provided with an insertion portion configured to be inserted into a subject, the insertion portion having a distal end provided with a sensor, the insertion portion having a cylindrical channel and a signal cable inserted therein, the signal cable being configured to be electrically connected to the sensor, the method comprising:
   dividing a plurality of signal lines to transmit a signal acquired by the sensor into a plurality of bundle portions;
   notching a part of a tube having heat shrinkability and an insulation property the notching excluding a portion of the tube in a circumferential direction of the tube to form one or more notches;
   cutting at least one end portion of the tube in a state where the tube is folded about each of the one or more notches to produce a first heat-shrinkable tube having a plurality of cylindrical portions, the plurality of cylindrical portions having end portions aligned in a longitudinal direction of the plurality of cylindrical portions;
   inserting the divided bundle portions into the plurality of cylindrical portions of the first heat-shrinkable tube, respectively;
   inserting the signal lines into a second heat-shrinkable tube, different from the first heat-shrinkable tube, the second heat-shrinkable tube having heat shrinkability and an insulation property;
   heating at least an overlapping portion of the first and second heat-shrinkable tubes in a state where the first and second heat-shrinkable tubes partially overlap each other to cause heat shrinkage of at least the overlapping portion;
   inserting the signal cable and the channel into a tubular portion having a tubular shape into which the signal cable and the channel are insertable; and
   connecting the tubular portion to a distal end housing provided at a distal end of the insertion portion, the distal end housing being configured to hold the sensor to form the distal end of the insertion portion.

2. The method of manufacturing the endoscope according to claim 1, wherein the one or more notches are formed by forming a wedge-shaped cutout in the tube.

3. The method of manufacturing the endoscope according to claim 1, wherein the one or more notches are formed by forming a circular cutout in the tube.

4. The method of manufacturing the endoscope according to claim 1, wherein
   the sensor is an ultrasound transducer, and
   the ultrasound transducer and the signal cable are electrically connected to each other.

5. The method of manufacturing the endoscope according to claim 1, wherein
   the sensor is an image sensor, and
   the image sensor and the signal cable are electrically connected to each other.

6. The method of manufacturing the endoscope according to claim 1, wherein at least the overlapping portion is heated to cause heat shrinkage in a state where a part of the second heat-shrinkable tube overlaps with a part of an insulating pipe extending from the distal end housing.

* * * * *